(12) United States Patent
Moehring

(10) Patent No.: US 6,464,994 B1
(45) Date of Patent: Oct. 15, 2002

(54) DIAPER DERMATITIS PREVENTATIVE MEDICATION AND A METHOD FOR MAKING AND USING SAME

(75) Inventor: Richard J. Moehring, Houston, TX (US)

(73) Assignee: Mentis Technologies, L.C., Houston, TX (US)

(*) Notice: Subject to any disclaimer, the term of this patent is extended or adjusted under 35 U.S.C. 154(b) by 0 days.

(21) Appl. No.: 09/577,633

(22) Filed: May 24, 2000

Related U.S. Application Data

(60) Provisional application No. 60/187,287, filed on Mar. 6, 2000, and provisional application No. 60/177,018, filed on Jan. 19, 2000.

(51) Int. Cl.[7] .................. A01N 25/34; A61K 6/00; A61K 9/00; A61F 13/15
(52) U.S. Cl. ............... 424/402; 424/401; 424/400; 424/78.01; 514/865; 604/358
(58) Field of Search .................. 424/402, 401, 424/400, 78.01; 514/865; 604/358

(56) References Cited

U.S. PATENT DOCUMENTS

| | | | |
|---|---|---|---|
| 4,438,102 A | | 3/1984 | Ganci |
| 4,454,159 A | | 6/1984 | Musher |
| 4,556,560 A | * | 12/1985 | Buckingham et al. |
| 5,091,193 A | | 2/1992 | Enjolars er al. |
| 5,871,763 A | * | 2/1999 | Luu et al. |
| 6,066,673 A | * | 5/2000 | McIver et al. |
| 6,190,894 B1 | * | 2/2001 | Thornfeldt |

OTHER PUBLICATIONS

Lintner, Carl J. Pharmaceutical Product Stability. pp. 141–238.
Buckingham, KW and Berg RW. Etiologic Factors in Diaper Dermatitis: The Role of Feces. Pediatric Dermatology. 3 (2): 107–12, Feb. 1986.
Rasmussen, JE. Classification of diaper dermatitis: an overview. Pediatrician 14 Suppl 1: 6–10, 1987. Abstract Only.

* cited by examiner

*Primary Examiner*—Thurman K. Page
*Assistant Examiner*—Isis Ghali
(74) *Attorney, Agent, or Firm*—Kohn & Associates

(57) ABSTRACT

The invention discloses a composition for the prevention and treatment of diaper dermatitis which includes an effective amount of an anti-lipase agent and/or an anti-protease agent in a suitable vehicle. The composition is designed to maintain an effective amount of the lipase and/or protease inhibitors and to be applied to tissues susceptible to fecal enzyme insult. The invention also discloses a composition for the prevention and treatment of diaper dermatitis which includes an effective amount of a sacrificial lipase substrate and/or, a sacrificial protease substrate in a suitable vehicle. The composition is designed to maintain an effective amount of the substrates and to be applied to tissues susceptible to fecal enzyme insult. The present invention also discloses a combination or mixtures of an effective amount of an anti-lipase agent and/or an anti-protease agent in a suitable vehicle and an effective amount of a sacrificial lipase substrate and/or a sacrificial protease substrate in a suitable vehicle.

13 Claims, No Drawings

DIAPER DERMATITIS PREVENTATIVE MEDICATION AND A METHOD FOR MAKING AND USING SAME

RELATED APPLICATIONS

This application claims priority to U.S. Provisional Patent Application Ser. No. 60/177,018 filed Jan. 19, 2000 and No. 60/187,287 filed Mar. 6, 2000, incorporated herein by reference.

BACKGROUND OF THE INVENTION

1. Field of the Invention

The present invention relates to a composition for the prophylaxis and/or treatment of diaper dermatitis or similar dermal irritation and methods for making and using the composition.

More particularly, the present invention relates to a composition including an enzyme inhibitor system, a sacrificial substrate system or a combined system for the prophylaxis and/or treatment of tissue irritation due to enzyme activity, especially protease and lipase enzyme activity, and methods for making and using such compositions. The compositions of the present invention are especially useful in inhibiting the activity of lipase and protease enzymes present in expressed feces that cause diaper dermatitis or similar dermal conditions or in tissues exposed to bodily fluids or any fluid containing lipase and protease enzymes or the exposure of tissues to any composition (solid, liquid, emulsion, dispersion, etc.) containing lipase and protease enzymes.

2. Description of the Related Art

Diaper dermatitis is a phenomenon frequently encountered by parents of small children or by patients in nursing homes who are required to wear a diaper. Although the dermatitis is treatable, occurrence and persistence often results in unhappy children and sleep deprived parents. In severe cases, it results in painful decubitus ulcers. Many ointments and powders exist on the market for treating and preventing diaper dermatitis, but most function by merely forming a barrier between the skin and expressed feces.

Thus, it would represent an advancement in the art to provide compositions and methods for their preparation and use which prevent the chemical and biological reactions that cause diaper dermatitis.

SUMMARY OF THE INVENTION

The present invention addresses these needs by providing a composition for treating or preventing diaper dermatitis, where the composition includes an enzyme inhibitor system, a sacrificial substrate system or mixtures or combinations thereof. The inhibitor system inhibits enzymatic activity caused by human feces that comes in contact with a portion of skin of a human adult or child after fecal expression or to deactivate enzymes in fecal matter that can irritate skin. Preferably, the enzyme inhibitor system includes a lipase inhibitor and/or a protease inhibitor or compounds capable of deactivating either lipases and/or proteases present in fecal matter. The sacrificial substrate system decreases or prevents enzymatic attack of portions of skin of the animal or human (adult or child) that comes in contact with expressed fecal material. Preferably, the sacrificial substrate system includes a lipase substrate and/or a protease substrate.

The present invention also provides a medication including a therapeutically effective amount of an enzyme inhibitor system, a sacrificial substrate system or mixtures or combinations thereof in a carrier, where the inhibitor system inhibits enzymatic activity caused by human feces that comes in contact with a portion of skin of a human adult or child after fecal expression and the sacrificial substrate system decreases or prevents enzymatic attack of portions of skin of the animal or human (adult or child) that comes in contact with expressed fecal material.

The present invention also provides a topical ointment including a therapeutically effective amount of an enzyme inhibitor system, a sacrificial substrate system or mixtures or combinations thereof in a carrier, where the inhibitor system inhibits enzymatic activity caused by human feces that come in contact with a portion of skin of a human adult or child after fecal expression and the sacrificial substrate system decreases or prevents enzymatic attack of portions of skin of the animal or human (adult or child) that comes in contact with expressed fecal material.

The present invention also provides a medicated powder including a carrier powder and a therapeutically effective amount of an enzyme inhibitor system, a sacrificial substrate system or mixtures or combinations thereof, where the inhibitor system is designed to inhibit enzymatic activity caused by human feces that comes in contact with a portion of skin of a human adult or child after fecal expression and the sacrificial substrate system decreases or prevents enzymatic attack of portions of skin of the animal or human (adult or child) that comes in contact with expressed fecal material.

The present invention also provides a wipe including a therapeutically effective amount of an enzyme inhibitor system, a sacrificial substrate system or mixtures or combinations thereof contained in a composition deposited on an outer surface or incorporated within the matrix or composition of the wipe, where the inhibitor system is designed to inhibit enzymatic activity caused by human feces that comes in contact with a portion of skin of a human adult or child after fecal expression and the sacrificial substrate system decreases or prevents enzymatic attack of portions of skin of the animal or human (adult or child) that comes in contact with expressed fecal material.

The present invention also provides a disposable diaper (adult or infant) including a therapeutically effective amount of an enzyme inhibitor system, a sacrificial substrate system or mixtures or combinations thereof contained in a composition deposited on an outer surface layer or incorporated within the matrix or compositions of the diaper, where the inhibitor system is designed to inhibit enzymatic activity present in human feces that comes in contact with a portion of skin of a human adult or child after fecal expression and the sacrificial substrate system decreases or prevents enzymatic attack of portions of skin of the animal or human (adult or child) that comes in contact with expressed fecal material.

The present invention also provides disposable training pants including a therapeutically effective amount of an enzyme inhibitor system, a sacrificial substrate system or mixtures or combinations thereof contained in a composition deposited on an outer surface layer or incorporated within the matrix or compositions of the training pants, where the inhibitor system is designed to inhibit enzymatic activity, preferably lipase and protease activity, present in human feces that comes in contact with a portion of skin of a human adult or child after fecal expression and the sacrificial substrate system decreases or prevents enzymatic attack of portions of skin of the animal or human (adult or child) that comes in contact with expressed fecal material.

The present invention further provides a method for preventing or treating diaper dermatitis including the step of contacting an area of skin of an adult or child in frequent contact with expressed feces with a composition including an effective amount of an enzyme inhibitor system, a sacrificial substrate system or mixtures or combinations thereof, where the composition inhibits or reduces skin irritation and the resulting dermatitis caused by fecal enzymes.

The present invention further provides a method for preventing or treating diaper dermatitis including the step of applying a composition including an effective amount of an enzyme inhibitor system, a sacrificial substrate system or mixtures or combinations thereof, where the composition reduces irritation and the resulting dermatitis of areas of skin of an adult or child in frequent contact with expressed feces due to enzymes present in fecal matter.

The present invention further provides a method for preventing or treating diaper dermatitis including the step of administering a composition including an effective amount of an enzyme inhibitor system, a sacrificial substrate system or mixtures or combinations thereof, where the composition reduces irritation and the resulting dermatitis of areas of skin of an adult or child in frequent contact with expressed feces due to enzymes present in fecal matter.

The present invention further provides a method for preventing or treating diaper dermatitis including the step of periodically administering a dose of a composition of the present invention sufficient to inhibit or reduce diaper dermatitis.

The present invention further provides a method for preparing a composition for preventing or treating diaper dermatitis including the step of mixing into a physical and/or chemical carrier an effective amount of an enzyme inhibitor system system, a sacrificial substrate system or mixtures or combinations thereof.

DETAILED DESCRIPTION OF THE INVENTION

The inventor has found that a general purpose compositions or medications for treating dermatitis or tissue irritation caused by exposure to expressed fecal material or bodily fluids containing certain enzymes can be prepared wherein the compositions or medications includes enzyme inhibitors, sacrificial enzyme substrates or mixtures or combinations thereof. The compositions or medications are designed either to reduce or eliminate enzymatic activity by deactivating enzymes found in fecal matter and/or to reduce or eliminate enzymatic activity directed to the skin or other tissue sites by providing a suitable competitive substrate upon which the enzymes can act in lieu of attacking the skin or tissue site. The medications of the present invention can be used on humans or animals to reduce skin irritation and the resulting dermatitis which often accompanies exposure to fecal matter or to reduce tissue irritation, and damage resulting from the exposure to bodily fluids containing lipase or protease enzymes.

The inventor has found that fecal matter contains, in addition to many other components, enzymes that are instrumental in skin irritation and ultimately in the formation of an adverse dermal response or dermatitis. The inventor has found that lipase and/or protease activity in fecal matter are key elements responsible for skin irritation in humans.

Broadly, the present invention relates to a composition including an effective amount or dosage of enzyme inhibitors and especially lipase and protease inhibitors or anti-lipase agents and anti-protease agents sacrificial enzyme substrates or mixture or combinations thereof, where the composition is designed to inhibit, reduce or substantially eliminate dermatologic effects from encountered feces, especially from pancreatic/gastric lipases and proteases.

This invention is based on the cause and effect relationship between diaper dermatitis or rash and the presence of enzymes, especially lipases and proteases in feces and presents an effective enzyme inactivating composition including an anti-lipase agent and/or anti-protease agent, an effective competitive enzyme substrate or mixtures or combinations thereof to provide prophylaxis and treatment of diaper dermatitis. The compositions of the present invention can also include adjuvants, excipients and other additives.

The present invention broadly relates to a method for inhibiting diaper dermatitis caused by skin exposure to feces including the step of administering according to a given protocol, a composition including an effective amount of enzyme inactivating agents to reduce, inhibit or substantially eliminate fecal enzyme activity. The present invention also relates to a method for treating diaper dermatitis caused by skin exposure to feces including the step of administering according to a given protocol a composition including an effective amount of enzyme inactivating agents to reduce, inhibit or substantially eliminate fecal enzyme activity and allow or facilitate skin healing.

The present invention also broadly relates to a method for inhibiting or preventing diaper dermatitis caused by skin exposure to feces including the step of administering according to a given protocol, a composition including an effective amount of a sacrificial enzyme substrate system to reduce, inhibit or substantially eliminate fecal enzyme activity on the skin of an animal. The present invention also relates to a method for treating diaper dermatitis caused by skin exposure to feces including the step of administering according to a given protocol a composition including an effective amount of a sacrificial enzyme substrate system to reduce, inhibit or substantially eliminate fecal enzyme activity on the skin of an animal and allow or facilitate skin healing.

The present invention also relates broadly to a method for inhibiting or preventing diaper dermatitis caused by skin exposure to feces including the step of administering according to a given protocol, a combination or mixture of a composition including an effective amount of enzyme inactivating agents and a composition including an effective amount of a sacrificial enzyme substrate system.

The relationship between fecal enzymes and diaper dermatitis was the subject of an experimental investigation: "Etiologic Factors in Diaper Dermatitis: The Role of Feces," Buckingham, K. W., Berg, R. W. Pediatric Dermatology, Vol. 3 107–122, incorporated herein by reference.

Sacrificial Substrate Systems

Lipase, previously described in the present invention, addresses a class of enzymes belonging to the esterases. A suitable sacrificial substrate would be hydrolyzable fat, for example as represented in ester form, such as synthetic or natural glyceride derivatives, yielding fatty acids and glycerol. Specific examples of suitable natural substrates would be Penut oil, Olive oil, Castor oil, and the like.

Proteases, (i.e., proteinases and peptide hydrolases), represent an even larger group of enzymes. The overall reaction is essentially the same in all peptidases and proteinases, and they do not have a substrate specificity in the ordinary sense; most of the enzymes in this group attack all denatured and many native proteins. These enzymes will hydrolyze single amino acids from the N-terminus of peptide chains, those hydrolyzing single residues from the C-terminus, those specific for dipeptide substrates, and those splitting off dipeptide units from either the N-terminus or the C-terminus. It should be noted that suitable substrates for this group is as varied as the diversity in this enzyme class. Suitable specific substrates would be natural and synthetic preparations of amino acid residues, Gastrins, Gelatins and the like.

The present invention is also directed to molecular substrates within a broad class of compounds which act as both Lipases and Proteases substrates. These bifunctional substrates possess both fatty acid and amino acid moiety or residue. Examples of these compounds are found in Lecithins, Amino acid bound Cephalins and the like. Examples of this group are available synthetically; Phosphotidylserine, Phosphotidylcholine, Phosphotidylethanolamine and the like. Natural substrates are found in Oil of Egg Yolk which contains fatty glycerides, cholesterol and lecithin. The glyceride fraction is a mixture of the glycerides of saturated and unsaturated fatty acids. Oleic, Linoleic, Palmitic, Stearic and Clupanodonic acids have been isolated from both the glyceride and lecithin fractions.

As can be appreciated from the presented information, suitable sacrificial substrates are numerous and diverse. The ratios of the above sacrificial groups can be compounded to reflect the anticipated concentration and demographic of the offending fecal borne enzymes.

Enzyme Inhibitor Systems

The enzyme inhibitor systems for use with the sacrificial enzyme substrate system of the present invention also ideally suitable in any application where lipase and/or protease activity can cause difficulties or may need to be inactivated such as during certain surgical procedures including pancreatic or bowel surgeries where the composition can be formulated into an irrigant to irrigate the tissues exposed to the lipase rich pancreatic excreations.

One class of fecal enzymes that the present invention is designed to inhibit are lipases, including pancreatic lipase. Pancreatic lipase is a single chain glycoprotein of 449 amino acids. It functions in dietary absorption by hydrolyzing triglycerides on the lipid water boundary surfaces of micelles. It has been shown that enzymatic activity is lost after chemical modification of Ser-152 in the porcine enzyme, indicating that this residue is essential for its catalytic activity. Ser-152 is located in the larger N-terminal domain at the C-terminal edge of a doubly wound parallel beta sheet and is part of an Asp-His-Ser triad, which is chemically analogous to, but structurally different from, that in serine proteases. This putative hydrolytic site is covered by a surface loop or flap and is generally inaccessible to the solvent. Interfacial activation, a characteristic property of lipolytic enzymes acting on water-insoluble substrates at water-lipid interfaces, is thought to involve re-orientation of this flap leading to catalytic activity. The same mechanism is thought to operate not only in pancreatic lipases, but in other lipases as well.

Beside lipases, the compositions of the present invention are also designed to inhibit proteases which are also known or suspected to contribute to diaper dermatitis.

Suitable lipase inhibitors include, without limitation, esterase inhibitors such as esterastin, lipstatin, valilactone and tetrahydrolipstatin which belong to a family of esterase inhibitors isolated from streptomyces strains and panclicins and ebelactones as well as other agents that effectively inhibit lipase activity and do not cause skin irritation or dermatitis, such as garlic extracts containing ajoene or mixtures or combinations thereof. Chemically, these inhibitors are derived from a group of mycolic acids, which are hydroxyfatty acids possessing a 2-alkyl substituent. The mycolic acid moiety of esterase inhibitors contains hydroxy groups in 3 and 5 positions. The 3-hydroxy group forms a beta lactone and the 5-hydroxy group is esterified with an amino acid such as N-acetyl-1-asparagine, N-formyl-1-leucine and N-formyl-1-valine. The asparagine derivative is esterastin; the leucine derivative is lipstatin; and the valine derivative is valilactone. Tetrahydrolipstatin, a hydrogenated product of lipstatin, possesses the same beta lactone ring present in esterastin, lipstatin and valilactone and has been shown to inhibit gastric and carboxy ester lipases in addition to pancreatic lipase. Lipstatin and tetrahydrolipstatin (tradenames Orlistat or Xenical) are known to irreversibly bind to the surface Ser site of different lipases, thereby inhibiting catalytic activation and activity. The long mycolic acid backbone in addition to beta-lactone ring is thought to promote interactions of these hydrophobic, amphipathic, water insoluble inhibitors with lipases.

Suitable anti-protease agents or protease inhibitors include, without limitation, a class of commercially available compounds known as Trypsin-Chymotrypsin inhibitors as well as other agents that effectively inhibit protease activity and do not cause skin irritation or dermatitis, or mixtures or combinations thereof.

Other Ingredients

The sacrificial substrates and/or enzyme inhibitor systems of the present invention can be used alone, but are preferably combined with other ingredients to form a composition suitable for administration in a given format. The compositions generally include the sacrificial substrates and/or enzyme inhibitor systems in a carrier. The carrier can be any combination of ingredient as set forth herein and can include other agents as well such as adjuvants, chemical excipients, or the like or mixtures or combinations thereof.

Suitable adjuvants, helping additives, include, without limitation, adjuvants that control pH and secondary therapeutic adjuvants including, without limitation:

anti-inflammatory agents such as antihistamines, corticosteroids, or the like, or mixtures or combinations thereof;

anti-microbial agents such as eugenol, guaiacol, zephiran chloride, or the like, or mixtures or combinations thereof;

antibiotic agents such as bacitracin, neomycin sulfate, gentamicin sulfate, erythromycin or the like, or mixtures or combinations thereof;

hemnostatics agents such as oxidized cellulose, thrombin, carboxymethylcellulose, or the like, or mixtures or combinations thereof;

anesthetic agents such as procaine, xylocaine, carbocaine, or the like, or mixtures or combinations thereof;

antifungal agents such as benzoic acid, salicylic acid, amphotericin B, miconazole, nistatin, toinaftate or the like or mixtures or combinations thereof;

other additives that can improve or enhance the therapeutic benefit of the compositions of this invention without interfering with the inhibiting activity of the enzyme inhibitors; or mixtures or combinations thereof or any of the above groups' listed adjuvants.

Adjuvants that control pH by neutralizing fecal components known to exacerbate the enzymatic insult of exposed or involved tissues, include, without limitation, effective concentrations of inorganic and organic buffers, (pK's from 2.0 to 6.0), to control pH between about 3.0 and about 7.0 such as carbonates, maleates, borates, citrates, adipates, or the like, or mixtures or combinations thereof. Controlling pH between about 3.0 and about 6.0 will prevent ammonia emission, neutralize bile acid/salt activity and help minimize enzyme activities. Weakly basic anion exchange resins of agarose, dextran, cellulose and polystyrene to sequester or augment neutralization of bile salt/acid and contribute to pH control, or mixtures or combinations thereof.

The composition of the present invention can include effective concentrations of the secondary therapeutic adjuvants to address the derivative effects of diaper dermatitis.

Suitable chemical excipients to solubilize, stabilize, emulsify and/or suspend the primary (enzyme inactivators), and secondary chemical or therapeutic components (adjuvants), include, without limitation, emulsifiers, surfactants, suspending agents, or mixtures or combinations thereof.

Emulsifiers increase the oil/water surface area, increasing kinetic interaction between the hydrophobic lipstatin and the amphiteric lipase. Suitable emulsifiers include, without limitation:

monomolecular films such as laurates, sorbitans, or the like, or mixtures or combinations thereof;

multimolecular films such as Acacia, gelatin, or the like, or mixtures or combinations thereof;

solid particle films such as bentonite or the like, or mixtures or combinations thereof;

surfactants such as natural or synthetic, anionic, cationic or nonionic surfactants, or mixtures or combinations thereof; or combinations or mixtures of the above-listed emulsifiers.

Concentrations of Enzyme Inhibits

Although the concentration of enzyme inhibitors in the compositions of the present invention can be sufficient to completely inactivate or inhibit a maximal enzyme concentration expected in feces, such a rationale based on solution mass action stoichiometry of fecal enzyme to inhibitor is not representative of the kinetics of the enzyme-inhibitor interaction to effectuate anti-dermatitis activity. The inventor has found that the enzyme-inhibitor interaction of interest is surface area limited. Therefore, the functional concentration of inhibitor to achieve a desired therapeutic result is expected to be much lower than that which would be predicted by mass action model. Notwithstanding the possible enzyme-inhibitor model active in diaper irritation and/or dermatitis, high inhibitor concentrations are generally used in the compositions of the present inventions including inhibitor concentrations up to a concentration limit of a particular carrier or vehicle. This approach is neither necessary nor efficient but provides for increased choice in preparing composition of the present invention. Of course, the composition should at least have an amount of enzyme inhibitor sufficient to ameliorate the symptoms of diaper dermatitis or to prevent its onset.

A theoretical calculation of an effective concentration of inhibitors required for complete inactivation of fecal enzyme can be determined by assuming that the maximum expected protease concentration in feces is about 100 mg per gram of feces having an activity of 10,000 units per mg protease. Under this assumption, an effective protease inhibitor concentration would be a dosage of about 40 mg of a trypsin inhibitor per gram of feces. Assuming, a maximum expected lipase activity of 150,000 units per mg lipase at a concentration of 5,000 mg per gram of feces, an effective lipase inhibitor concentration would be a dosage of about 60 mg of a lipase inhibitor such as tetrahydrolipstatin per gram of feces. Now assuming a given volume of feces for a child to be about 100 grams per expression, a composition having an available concentration of inhibitors of about 4 g trypsin inhibitor and about 6 g tetrahydrolipstatin per dose would be effective in inhibiting substantially all fecal lipase and protease activity. It should be recognized that these effective dosages are based on inhibiting or inactivating 100% of fecal lipase and/or protease activity. However, as stated above, such concentrations of inhibitors may not be necessary because it is only the lipase and protease concentrations that come into contact with the skin that are relevant. Thus, the compositions of the present invention can incorporate much lower concentration of the inhibitors and still render a desired therapeutic effect.

Concentrations of Enzyme Substrates

The concentrations of the specific enzyme substrates used in the compositions and/or formulations of the present invention can be the same as the concentration of the enzyme inhibitors discussed above. However, because the substrates are generally less expensive compounds, these compounds can be used in greater concentrations than the inhibitors. In fact, in some formulation, the enzyme substrate(s) could be the carrier or the vehicle in which the enzyme inhibitors are contained.

Formulations

The formulations of the present invention relates to one or both systems in a carrier. The carriers can also include porous and/or non-porous micro beads or structures designed to modify the physical states of the primary and/or secondary components and to provide controlled delivery rates and delivery sites.

Suspending agents aid in the interfacial kinetics of the enzyme/anti-enzyme mechanism. Structured vehicles are generally aqueous solutions of polymeric materials, such as the hydrocolloids. Typical examples are methylcellulose, carboxymethylcellulose, acacia and carbopols.

Stability information is ubiquitous and addresses effective preparations/protocols for controlling dosages, deliveries and vehicles. A comprehensive treatment of all aspects of pharmaceutical product stability has been published by C. J. Lintner: Quality Control in the Pharmaceutical Industry, vol.2, Academic Press, New York, 141, 1973, incorporated herein by reference.

The compositions of the present invention can be formulated into different vehicles including, without limitation, topicals, sequestering systems, aerosols, sprays or irrigants.

Suitable topical preparation include, without limitation, ointments, emulsions, suspensions, powders, or the like.

Suitable sequestering systems include, without limitation, diapers, wipes or the like. These systems provide mechanical sequestering, neutralization and removal of fecal enzymes and coincidental irritants. Illustrative examples into which effective concentrations of anti-enzyme agents and adjuvants may be delivered to the embodiments of a diaper and/or wipe can be provided through mechanical processing such as absorption, adsorption, impregnation, encapsulation or chemical binding such polymerization, covalency or the like.

Aerosols, sprays and irrigants are solutions, emulsions, dispersions or suspensions of viscosities approximating water, complementing tonic physiologic status and containing effective amounts of anti-enzyme agents and desired adjuvants may be delivered through the embodiments of single/multiphase systems contained within aerosol, spray or irrigating dispensers.

The compositions of this invention can also employ a performance indicator to monitor the functionality of the chemical matrix, the delivery system or vehicle or the activity of the enzyme inhibitors at the time of use. Such a system can employ recognizable schemes to qualify the integrity of both anti-enzyme components, adjuvants and delivery systems.

Several illustrative examples of topical formulations into which therapeutically effective concentrations of anti-enzyme agents, and optional adjuvants my be admixed, follow:

1. Simple ointment, oleaginous:
   white wax 25 g
   yellow wax 25 g
   petrolatum 950 g
   The proportion of wax can be varied to obtain a suitable consistency of the ointment.
2. Hydrophilic Petrolatum (this preparation will absorb large amount of water of aqueous solutions of active ingredient, form water-in-oil type emulsions):
   Cholesterol 30 g
   stearyl alcohol 30 g
   white wax 80 g
   white petrolatum 860 g
3. Lanolin, Hydrous or anhydrous wool fat.
4. Washable Hydrophilic Ointment (oil-in-water emulsion):
   methylparben 0.025 g
   propylparben 0.015 g
   sodium lauryl sulfate 10 g
   propylene glycol 120 g
   stearyl alcohol 250 g
   white petrolatum 250 g
   purified water 370 g
5. Polyethylene Glycol Ointment:
   polyethylene glycol 3350 350 g
   polyethylene glycol 400 600 g
   stearyl alcohol 50 g
6. Absorbent dusting powders
   Magnesium stearate 100 g
7. Absorbent dusting powders:
   Magnesium stearate 50 g
   Boric Acid 50 g
8. Absorbent/adsorbent Delivery Particles:
   Mixtures of porous and non-porous micro beads.

The formulations listed above are for illustrative purposes only. Moreover, the treating protocol used to treat or prevent diaper dermatitis can include one or more of the compositions of the present invention as well as one or more of the formulations set forth above. Of course, to the vehicles shown above may be added the enzyme inhibitors or inactivators and/or the additional therapeutically effective adjuvants as set forth herein to address the effects of diaper dermatitis.

The compositions or formulations of this invention are generally prepared by mixing an effective amount of an enzyme inhibiting system alone or in conjunction with an adjuvant system into a desired vehicle under conditions of time, temperature and pressure to facilitate the formation of a substantially homogeneous composition. Generally, the mixing time is between about 0.1 minutes and about 1 hour, preferably between about 0.2 minutes and about 40 minutes and particularly between about 1 minute and about 30 minutes. Generally, the temperature is between about 50° F. and about 300° F., preferably between about 60° F. and about 200° F., and particularly about room temperature. Generally, the pressure is between about 0.5 atmosphere and about 25 atmospheres, preferably between about 1 atmosphere and about 5 atmospheres, and particularly at about standard atmospheric pressure. The mixing can be carried out in a traditional open mixer, a mixing extruder, a blender or any other mixing apparatus well-known in the art. Of course, the mixing time, mixing temperature and mixing pressure can be adjusted to the particular equipment being used provided that the temperature does not exceed a decomposition temperature for the inhibitors or any other component of the composition.

One ointment formulation including an enzyme inactivating system of the present invention for direct application to skin follows:
   8 g of cholestyramine (a weak anion resin)
   50 g of Euserin a water based glycerin carrier
   200 mg of tetrahydrolipstatin
   500 mg of trypsin-chymotrypsin inhibitor from Sigma Chemicals.

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

I claim:

1. A composition for treating enzyme induced tissue damage in an acidic environment comprising an effective amount of a treating system selected from the group consisting of a sacrificial lipase substrate including hydrolyzable fat, sacrificial protease, substrate including natural and synthetic preparations of amino acid residues, gastrins, and, gelatins, sacrificial lipase and protease substrate including bifunctional substrates having a fatty acid and amino acid moiety for decreasing enzyme activity, an enzyme inhibitor system, and combinations thereof, wherein the composition neutralizes acid activity.

2. The composition of claim 1, wherein the enzyme inhibitor system comprises a lipase inhibitor.

3. The composition of claim 2, wherein the lipase inhibitor is selected from the group consisting of esterastin, lipstatin, valilactone, tetrahydrolipstatin, panclicin, ebelactone, ajoene and mixtures or combinations thereof.

4. The composition of claim 1, wherein the enzyme inhibitor system comprises a protease inhibitor.

5. The composition of claim 4, wherein the protease inhibitor comprises a trypsin-chymotrypsin inhibitor.

6. The composition of claim 1, wherein the enzyme inhibitor system comprises a lipase inhibitor and a protease inhibitor.

7. The composition of claim 6, wherein the lipase inhibitor is esterastin, lipstatin, valilactone, tetrahydrolipstatin, panclicin, ebelactone, ajoene or mixtures or combinations thereof and the protease inhibitor is a trypsin-chymotrypsin inhibitor.

8. The composition of claim 1, further comprises effective concentrations of therapeutic adjuvants, where the therapeutic adjuvants comprises anti-inflammatory agents, anti-microbial agents, antiboitic agents, hemostatic agents, anaesthetic agents, anti-fungal agents or mixtures or combinations thereof.

9. The composition of claim 1, further comprises a performance indicator to monitor the integrity of the enzyme inhibitor system.

10. The composition of claim 1, further comprising a carrier.

11. A method for treating enzyme damage to tissue in an acidic environment by:
   administering to tissue of a subject an effective amount of an enzyme treating system, where the treating system is selected from the group consisting of a sacrificial lipase substrate including hydrolyzable fat, sacrificial protease substrate including natural and synthetic preparations of amino acid residues, gastrins and, gelatins, sacrificial lipase and protease substrate including bifunctional substrates having a fatty acid and amino acid moiety for decreasing enzyme activity, an enzyme inhibitor system, and combinations thereof, where the system neutralizes acid activity.

12. A method for treating enzyme damage to tissue in an acidic environment by:

periodically administering to a tissue of a subject an effective amount of an enzyme treating system, where the treating system is selected from the group consisting of a sacrificial lipase substrate including hydrolyzable fat, sacrificial protease substrate including natural and synthetic preparations of amino acid residues, gastrins, and, gelatins, sacrificial lipase and protease substrate including bifunctional substrates having a fatty acid and amino acid moiety for decreasing enzyme activity, an enzyme inhibitor system, and combinations thereof, where the system neutralizes acid activity.

13. A method for preparing a composition for treating enzyme damage to tissue in an acidic environment by:

mixing an effective amount of an enzyme treating system selected from the group consisting of a sacrificial lipase substrate including hydrolyzable fat, sacrificial protease substrate including natural and synthetic preparations of amino acid residues, gastrins, and, gelatins, sacrificial lipase and protease substrate including bifunctional substrates having a fatty acid and amino acid moiety for decreasing enzyme activity, an enzyme inhibitor system and combinations thereof into a vehicle, where the system neutralizes acid activity.

* * * * *